United States Patent
Lyons et al.

(10) Patent No.: US 6,960,232 B2
(45) Date of Patent: Nov. 1, 2005

(54) ARTIFICIAL INTERVERTEBRAL DISC

(75) Inventors: Matthew Lyons, Wilberham, MA (US); Stephen M. Green, Syracuse, NY (US); Matthew A. Keary, Etna, NY (US)

(73) Assignee: Blackstone Medical, Inc., Springfield, MA (US)

(*) Notice: Subject to any disclaimer, the term of this patent is extended or adjusted under 35 U.S.C. 154(b) by 67 days.

(21) Appl. No.: 10/423,414

(22) Filed: Apr. 25, 2003

(65) Prior Publication Data

US 2004/0034423 A1 Feb. 19, 2004

Related U.S. Application Data

(60) Provisional application No. 60/375,842, filed on Apr. 25, 2002.

(51) Int. Cl.[7] ................................................ A61F 2/44
(52) U.S. Cl. ............................. 623/17.16; 623/17.11; 623/17.15
(58) Field of Search .......................... 623/17.11, 17.12, 623/17.13, 17.14, 17.15, 17.16

(56) References Cited

U.S. PATENT DOCUMENTS

| | | | |
|---|---|---|---|
| 4,309,777 A | | 1/1982 | Patil |
| 4,349,921 A | | 9/1982 | Kuntz |
| 4,554,914 A | | 11/1985 | Kapp et al. |
| 4,759,769 A | | 7/1988 | Hedman et al. |
| 4,911,718 A | | 3/1990 | Lee et al. |
| 4,932,975 A | | 6/1990 | Main et al. |
| 4,997,432 A | | 3/1991 | Keller |
| 5,071,437 A | | 12/1991 | Steffe |
| 5,123,926 A | | 6/1992 | Pisharodi |
| 5,171,281 A | | 12/1992 | Parsons et al. |
| 5,236,460 A | | 8/1993 | Baber |
| 5,258,031 A | | 11/1993 | Salib et al. |
| 5,306,310 A | | 4/1994 | Siebels |
| 5,314,477 A | | 5/1994 | Marnay |
| 5,370,697 A | * | 12/1994 | Baumgartner ............ 623/17.15 |
| 5,401,269 A | | 3/1995 | Buttner-Janz et al. |
| 5,480,447 A | * | 1/1996 | Skiba ....................... 623/21.19 |
| 5,507,816 A | | 4/1996 | Bullivant |
| 5,507,823 A | * | 4/1996 | Walston et al. .......... 623/23.41 |
| 5,534,030 A | | 7/1996 | Navarro et al. |
| 5,545,229 A | | 8/1996 | Parsons et al. |
| 5,549,679 A | | 8/1996 | Kuslich |
| 5,674,294 A | * | 10/1997 | Bainville et al. ......... 623/17.16 |
| 5,674,296 A | | 10/1997 | Bryan et al. |
| 5,676,701 A | | 10/1997 | Yuan et al. |
| 5,683,465 A | | 11/1997 | Shinn et al. |
| 5,702,449 A | | 12/1997 | McKay |
| 5,702,450 A | | 12/1997 | Bisserie |
| 5,865,846 A | * | 2/1999 | Bryan et al. ................. 128/898 |
| 5,899,941 A | | 5/1999 | Nishijima et al. |
| 6,001,130 A | | 12/1999 | Bryan et al. |
| 6,156,067 A | | 12/2000 | Bryan et al. |
| 6,264,695 B1 | * | 7/2001 | Stoy ........................ 623/17.16 |
| 6,419,706 B1 | * | 7/2002 | Graf ........................ 623/17.16 |
| 6,626,943 B2 | | 9/2003 | Eberlein et al. |
| 6,692,495 B1 | * | 2/2004 | Zacouto ....................... 606/61 |
| 6,743,511 B2 | | 6/2004 | Dittrich et al. |
| 6,749,635 B1 | | 6/2004 | Bryan |
| 2002/0035400 A1 | | 3/2002 | Bryan et al. |
| 2002/0128715 A1 | | 9/2002 | Bryan et al. |
| 2002/0151979 A1 | * | 10/2002 | Lambrecht et al. ...... 623/17.16 |
| 2003/0135277 A1 | | 7/2003 | Bryan et al. |
| 2003/0199982 A1 | | 10/2003 | Bryan |
| 2004/0054411 A1 | | 3/2004 | Kelly et al. |
| 2004/0098131 A1 | | 5/2004 | Bryan et al. |

FOREIGN PATENT DOCUMENTS

| | | |
|---|---|---|
| EP | 0 610 837 A1 | 8/1994 |
| WO | WO 91/13598 A1 | 9/1991 |
| WO | WO 94/04100 A1 | 3/1994 |

\* cited by examiner

*Primary Examiner*—Paul B. Prebliic
(74) *Attorney, Agent, or Firm*—Greenberg Traurig, LLP

(57) ABSTRACT

The present invention is directed to the field of prosthetic devices. More particularly, one embodiment of the present invention is directed to an artificial disc that can be used as a replacement for an intervertebral disc (e.g., a human intervertebral lumbar disc).

27 Claims, 11 Drawing Sheets

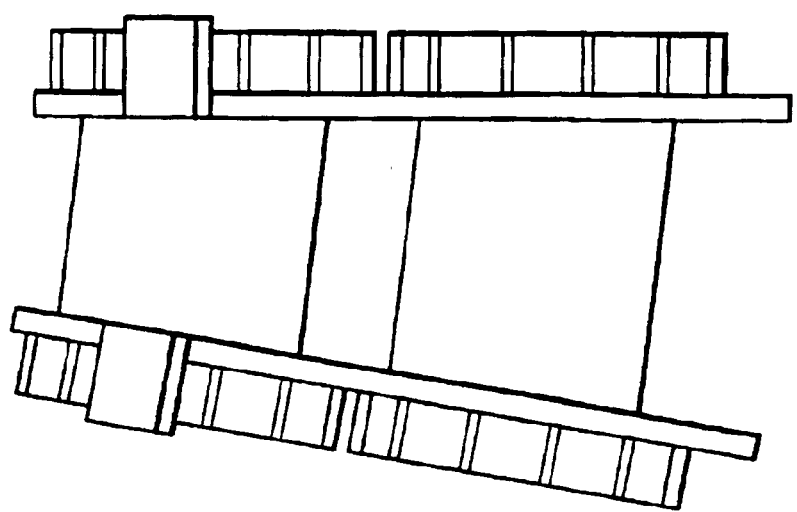
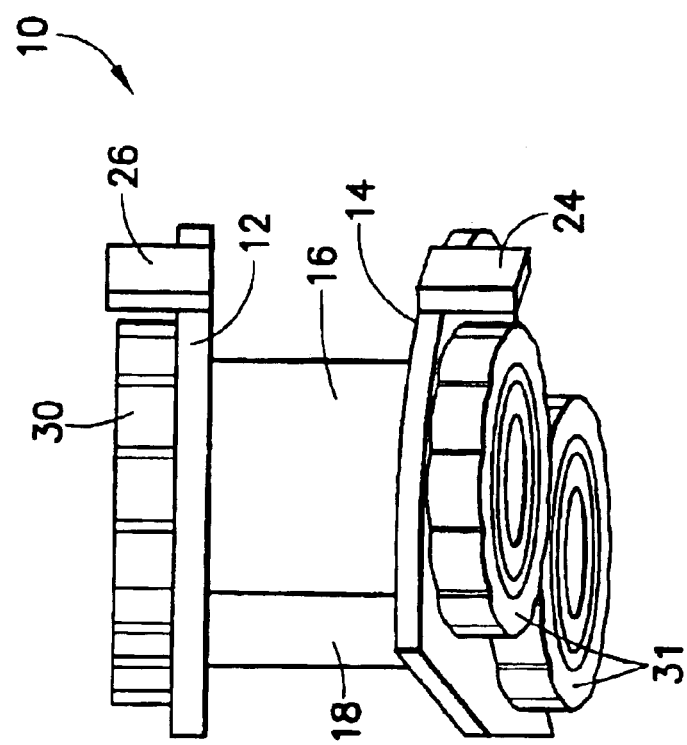
FIG. 3B
FIG. 3A

ARTIFICIAL INTERVERTEBRAL DISC

RELATED APPLICATIONS

This application claims the benefit under 35 U.S.C. 119(e) of U.S. Provisional Application Ser. No. 60/375,842 filed Apr. 25, 2002.

FIELD OF INVENTION

The present invention is directed to the field of prosthetic devices. More particularly, one embodiment of the present invention is directed to an artificial disc that can be used as a replacement for an intervertebral disc (e.g., a human intervertebral lumbar disc).

BACKGROUND OF THE INVENTION

As an alternative to spinal fusion techniques, numerous attempts have been made to design an artificial disc to replace an intervertebral lumbar disc that has become damaged or otherwise unhealthy. These devices have been reported to have attained varying degrees of success in performing functions of a healthy intervertebral disc and mimicking the behavior thereof (e.g., response to compressive forces applied to the spine and the preservation of proper kinematics of the spine).

SUMMARY OF THE INVENTION

The present invention provides an artificial intervertebral disc (AID) assembly. In one embodiment, the artificial disc assembly is comprised of first and second anchor plates, each of which has a vertebrae contacting side, and at least one column comprised of expanded poly (tetraflouroethylene) ("ePTFE") that is joined to the first and second anchor plates. The column may be a hollow column, or it may be a solid column. In yet another embodiment, the column may be filled with a compressible material, such as an elastomer. For example, the elastomer may be a silicone or a urethane or a thermoplastic elastomer. In yet another embodiment, the column may be solid ePTFE. In yet another embodiment of the present invention, the column of ePTFE may contain a compression element such as a spring constructed of a biocompatible material, such as titanium.

ePTFE is a well-known material processed from PTFE polymer. ePTFE has a network of nodes and fibrils that impart expandability, compressibility, and porosity (to name but a few of the properties possessed by ePTFE).

It is believed that the network of nodes and fibrils of an ePTFE structure, possibly combined with another spring-like material, presents very similar stress/strain behavior to that of a healthy, intervertebral disc (e.g., an intervertebral lumbar disc). That is, the amount of force per unit deflection needed to compress and/or elongate the ePTFE (e.g., in combination with another material) varies non-linearly (e.g., until the material is compressed to its solid height or the ePTFE is extended to full expansion of the nodes, at which point the modulus of elasticity increases still more rapidly, and the ePTFE stiffens). It is further believed that ePTFE allows for both compression and extension locally within the same structural member, which mimics the behavior of a disc (e.g., an intervertebral lumbar disc) in the modes of spinal extension, flexion, and lateral bending.

In yet another embodiment, the AID is constructed of first and second anchor plates, each of which has a vertebrae contacting side, and a plurality of columns of ePTFE that are joined to the first and second anchor plates. In one embodiment, two columns are joined to the anchor plates. In one embodiment, the columns may be filled with an elastic, compressible material, such as a silicone elastomer or urethane elastomer. In another embodiment, the column may be solid ePTFE.

In yet another embodiment, the prosthetic disc assembly is provided with anchor plates that have undercuts and/or tabs to facilitate the anchoring of the assembly to the vertebral bodies. The tabs may be provided with screw-holes into which bone screws can be inserted to anchor the assembly to the vertebral body. In yet another embodiment, the anchor plates may be assembled with the columns such that they are non-parallel (e.g., in order to provide a profile that substantially corresponds to the lordotic profile of the vertebral bodies). In another embodiment, the non-parallel angle may be 5° to 15°. In another embodiment, the final AID assembly may be provided with matching assemblies (e.g., a left and a right assembly), each assembly having first and second anchor plates and at least one column of ePTFE, that is joined to the anchor plates, the left and right assemblies being sized and dimensioned to reside adjacent to each other when positioned in the space between vertebral bodies.

In yet another embodiment, the AID is comprised of first and second anchor plates, each of which has a vertebrae contacting side, and at least one column comprised of ePTFE that is joined to the first and second anchor plates. Compression ferrules may join the column to the anchor plates. The ferrules may be fitted inside the column, and, as a result of the sizing of the ferrules relative to the sizing of the openings in the anchor plates, the ferrules impinge against the inner wall of the tube and force it outward against the walls of the anchor plates at their openings. As an alternative to joining the anchor plate to the columns with ferrules, the ends of the column may be flared and a compression flange affixed onto the anchor plate, trapping the ends of the column (once the column has been inserted through the anchor plates) in order to force the ends of the column axially into frictional engagement with the anchor plates.

In yet another embodiment, the assembly is comprised of first and second anchor plates and at least one column of ePTFE that is joined to the first and second anchor plates. The column may be chemically bonded to another element made, for example, from PTFE or ePTFE and then the column assembly may be captured by the anchor plate. As an alternative, the ePTFE may be heat-sealed or ultrasonically welded to another element made, for example, from PTFE or ePTFE and then the column assembly may be captured by the anchor plate. In another embodiment, the column may be impregnated with an elastomer such as urethane in order that the impregnated column can be bonded to another structure, thus allowing for termination to the anchor plate.

The materials used in constructing the implant may be biocompatible. The anchor plates, ferrules, compression flanges, and/or springs may be constructed of titanium 6AL4V ELI (extra low interstitial), a titanium alloy containing 6% aluminum and 4% vanadium. ePTFE, used to construct the columns, is a biocompatible material. Any additional elastomeric or non-elastomeric materials utilized in the assembly may be biocompatible.

It is contemplated that the artificial disc assembly of the present invention can be inserted with a posterior, lateral approach to the spine, as well as allowing for an anterior implantation approach.

In yet another embodiment, a thin coating of a silicone or urethane can be coated on the column of ePTFE to prohibit tissue growth on the column and within the interstices.

BRIEF DESCRIPTION OF THE DRAWINGS

FIG. 3A shows a side elevation view along one side of a component of an artificial intervertebral disc according to an embodiment of the present invention;

FIG. 3B shows a side elevation view along another side of a component of an artificial intervertebral disc according to an embodiment of the present invention;

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Figure 8:
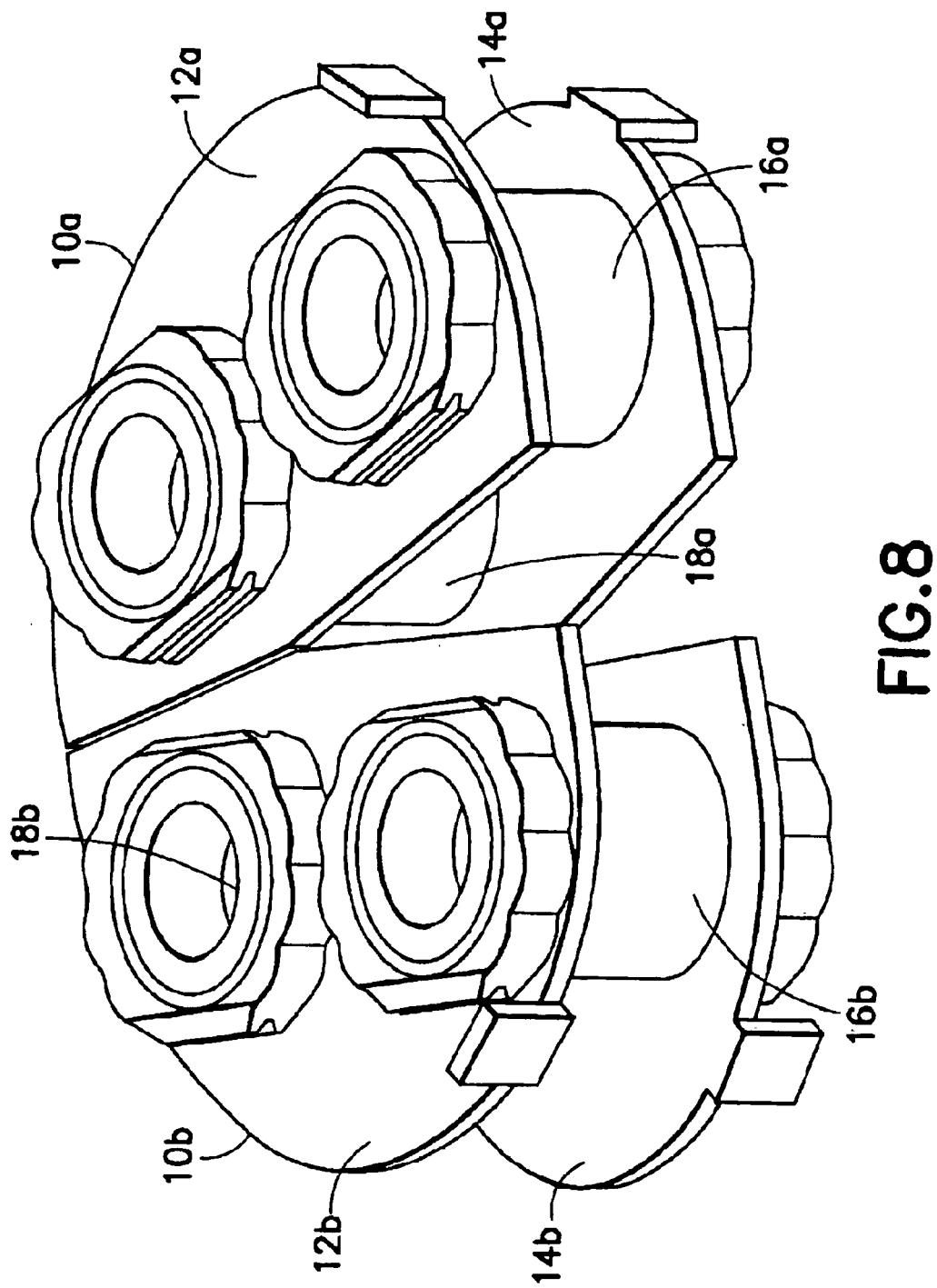
FIG. 8 shows a perspective view of another embodiment of the present invention in which the artificial intervertebral disc is comprised of a pair of implant components.

As discussed above, the artificial intervertebral disc of the present invention may be comprised of one or more components or assemblies. In this regard, it is noted that each Figure (excluding FIGS. 6 and 8) show views of assemblies which may be combined (as shown in FIG. 8, for example) to produce a final artificial intervertebral disc.

Figure 1:
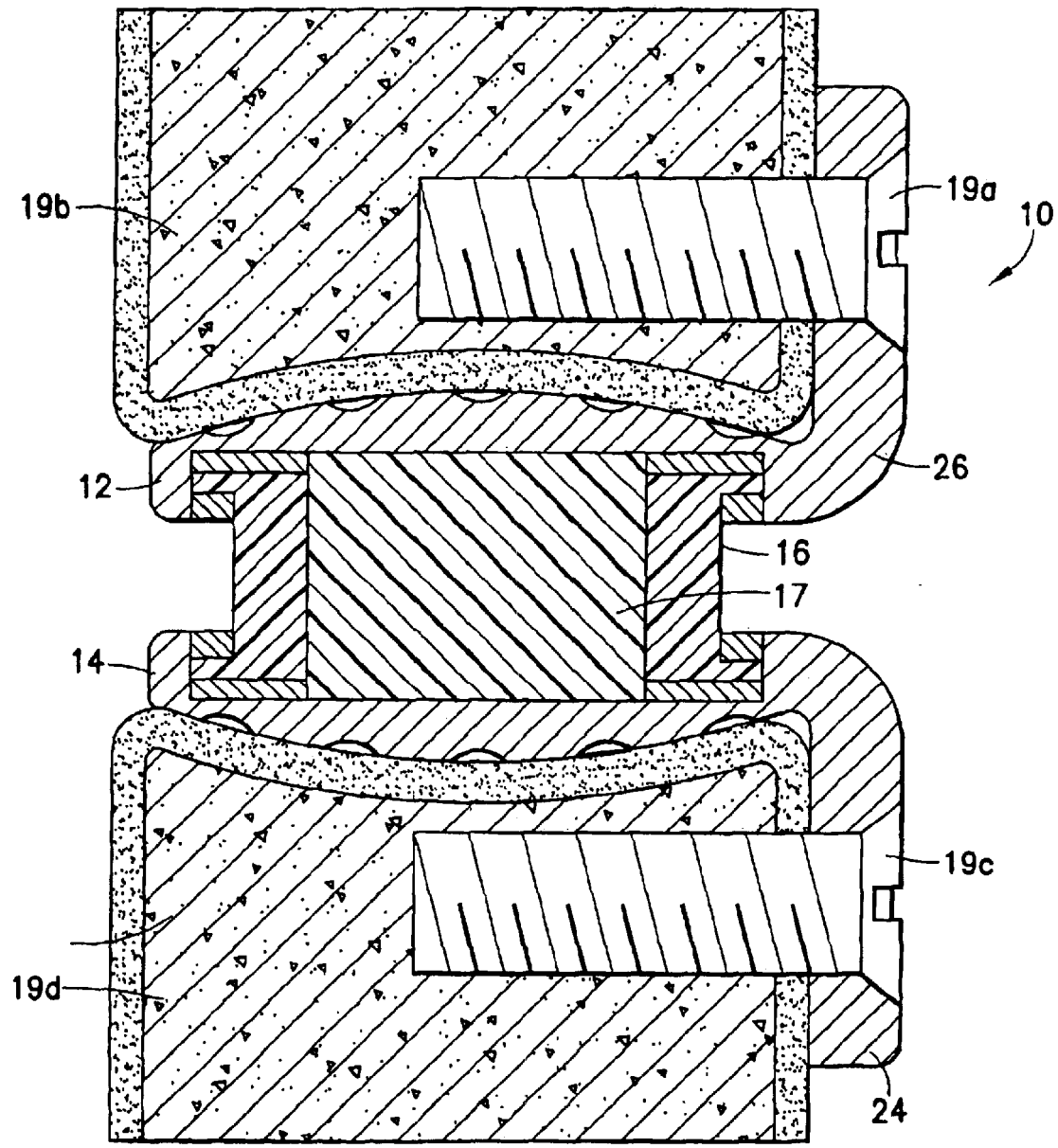
FIG. 1 shows a cross sectional view of a component of an artificial intervertebral disc according to an embodiment of the present invention.

Referring now to FIG. 1, an artificial intervertebral disc assembly according to an embodiment of the present invention is shown. As seen in this Figure, artificial intervertebral disc assembly 10 is comprised of a first anchor plate 12 and a second anchor plate 14, between which is disposed column 16. Column 16 (which is formed of ePTFE) includes therein column filler 17 (which is formed of an elastomer). Anchor plate 12 includes a mechanism (threaded fastener 19a) for attachment to a vertebral body 19b. Likewise, anchor plate 14 includes a mechanism (threaded fastener 19c) for attachment to a vertebral body 19d.

Figure 2A:
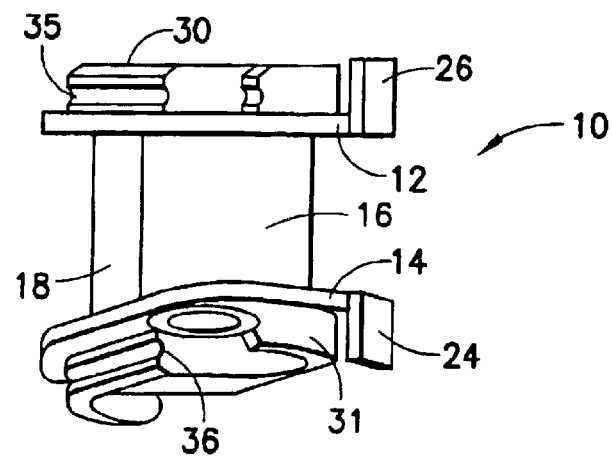
FIG. 2A shows a side elevation view along one side of a component of an artificial intervertebral disc according to an embodiment of the present invention.
Figure 2B:
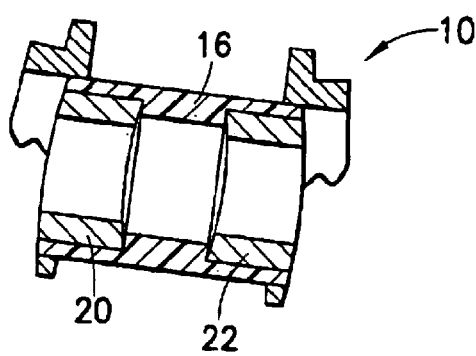
FIG. 2B shows a cross sectional view of a component of an artificial intervertebral disc according to an embodiment of the present invention.
Figure 2C:
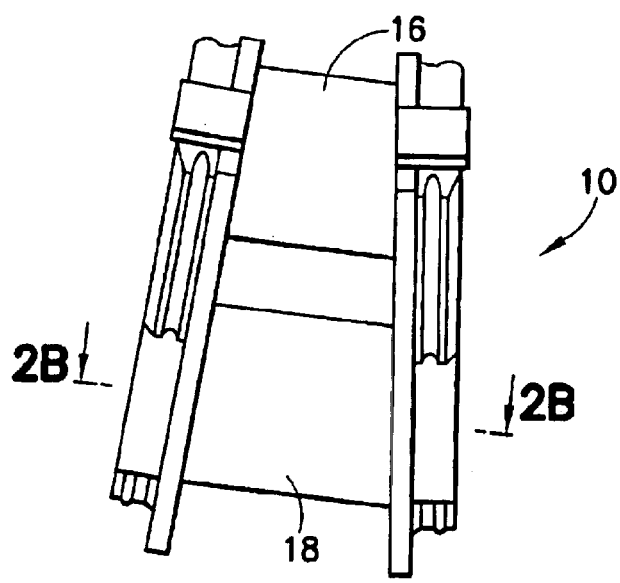
FIG. 2C shows a side elevation view along another side of a component of an artificial intervertebral disc according to an embodiment of the present invention.
Figure 2E:
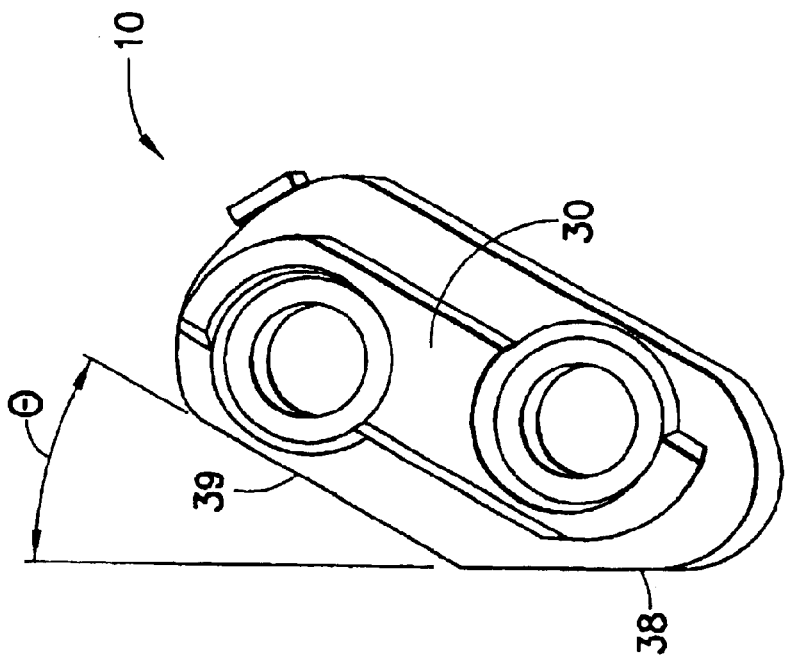
FIG. 2E shows a top plan view of a component of an artificial intervertebral disc according to an embodiment of the present invention.
Figure 2D:
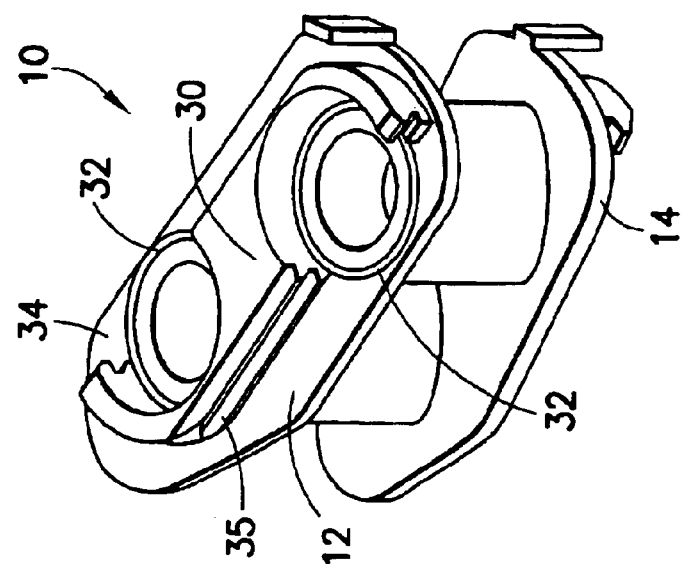
FIG. 2D shows a perspective view of a component of an artificial intervertebral disc according to an embodiment of the present invention.
Figure 3D:
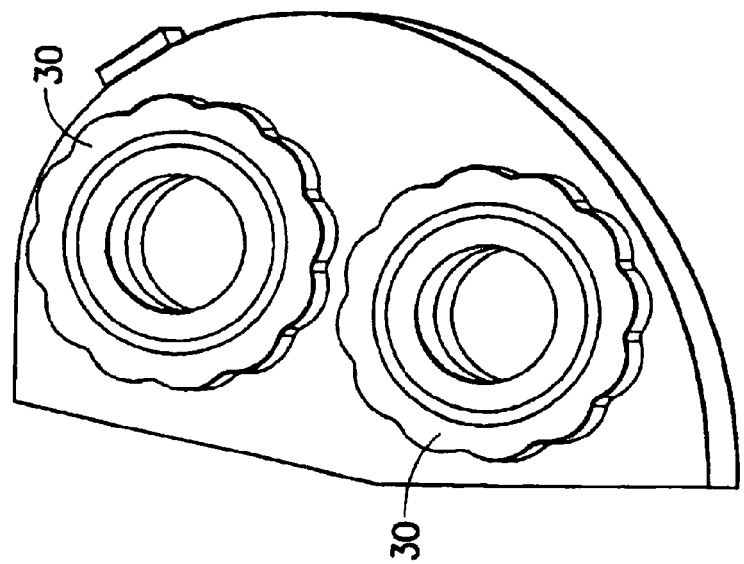
FIG. 3D shows a top plan view of an a component of an artificial intervertebral disc according to an embodiment of the present invention.
Figure 3C:
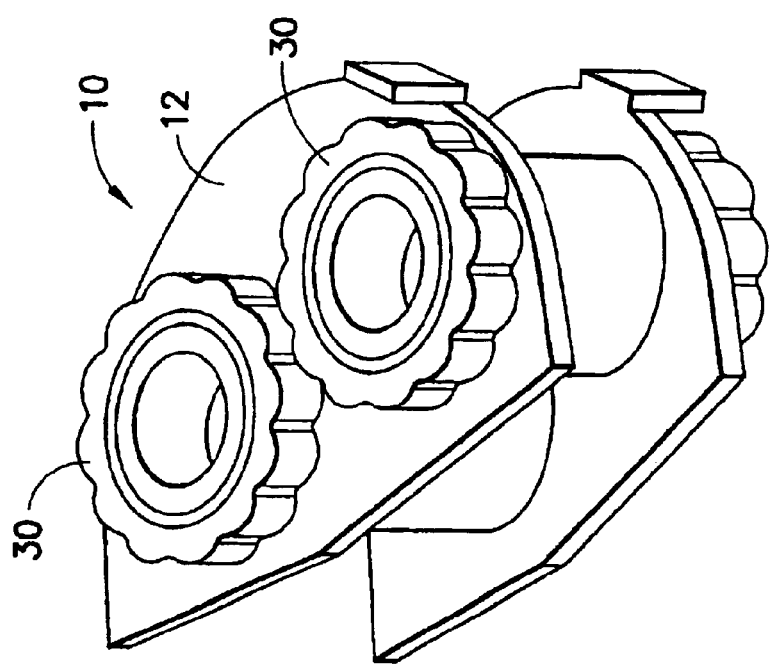
FIG. 3C shows a perspective view of a component of an artificial intervertebral disc according to an embodiment of the present invention.
Figure 4A:
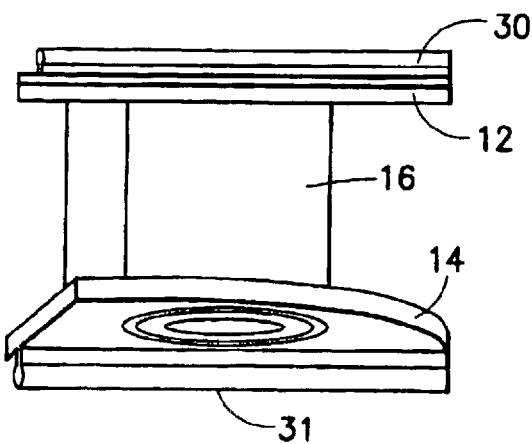
FIG. 4A shows a side elevation view along one side of a component of an artificial intervertebral disc according to an embodiment of the present invention.
Figure 4B:
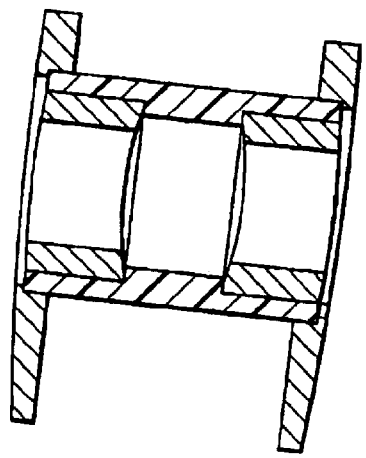
FIG. 4B shows a cross sectional view of a component of an artificial intervertebral disc according to an embodiment of the present invention.
Figure 4C:
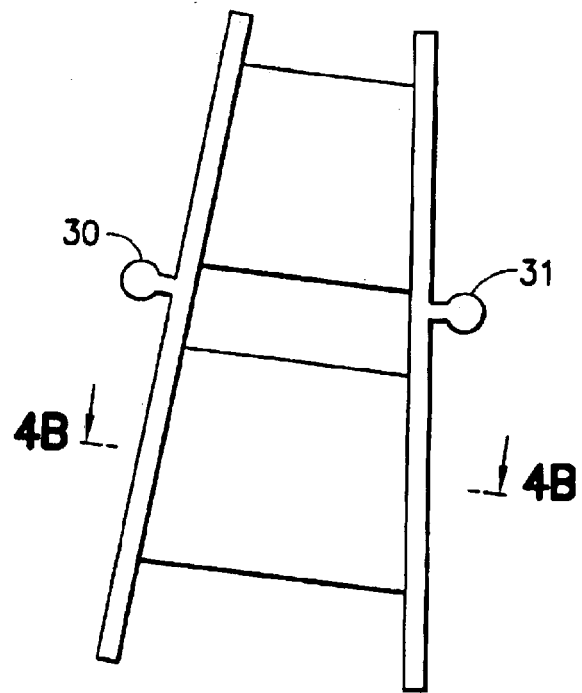
FIG. 4C shows a side elevation view along another side of a component of an artificial intervertebral disc according to an embodiment of the present invention.
Figure 4E:
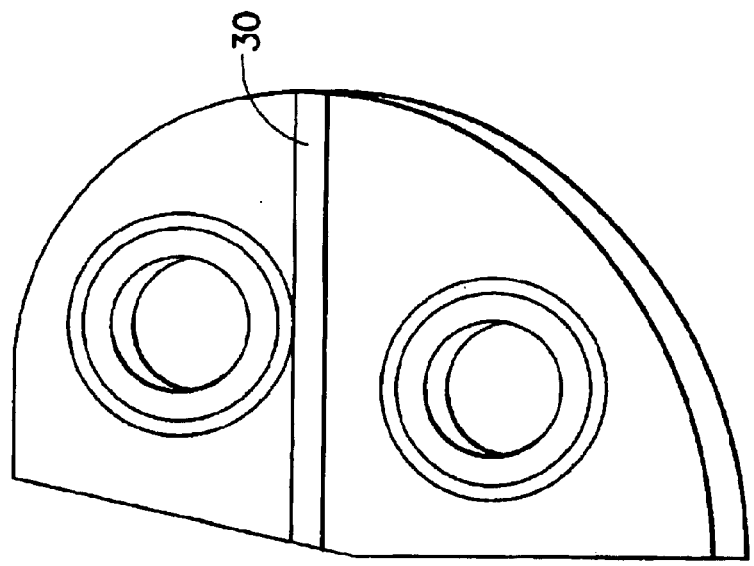
FIG. 4E shows a top plan view of a component of an artificial intervertebral disc according to an embodiment of the present invention.
Figure 4D:
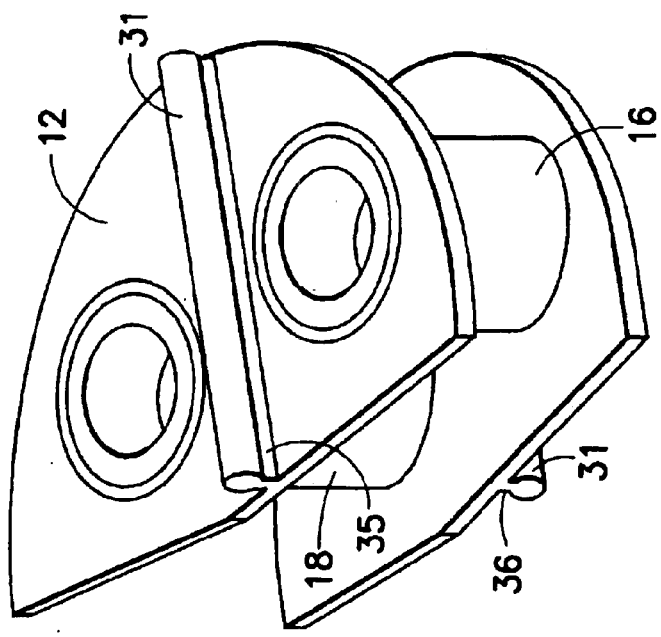
FIG. 4D shows a perspective view of a component of an artificial intervertebral disc according to an embodiment of the present invention.

Referring now to FIGS. 2A–2E, an artificial intervertebral disc assembly according to another embodiment of the present invention is shown. As seen in these Figures, the artificial disc assembly 10 has a first anchor plate 12, a second anchor plate 14 (both of which may be constructed of titanium, for example), and columns 16, 18 which are constructed of ePTFE. The columns 16, 18 serve as spacer elements which keep the anchor plates 12, 14 apart from each other. As shown in FIG. 2D, for example, the end surface 32 of columns 16, 18 terminate flush at the top surface 34 of anchor plate 12 (as well as flush at the bottom surface of anchor plate 14, which configuration is not shown in this view). The outer diameter of the column lies against the inner diameter of the opening in the anchor plate. A compression ferrule 20, 22 is placed within the column at an end thereof, as shown in FIG. 2B. The ferrule is sized to form a snug fit between the ferrule, column, and sidewalls defining the opening of the anchor plate. This forms a firm frictional engagement between the components that locks the columns in place.

In another embodiment, the ends of the columns may be flared and a compression flange affixed onto the anchor plate, trapping the ends of the column (once the column has been inserted through the anchor plates) in order to force the ends of the column axially into frictional engagement with the anchor plates.

Figure 7:
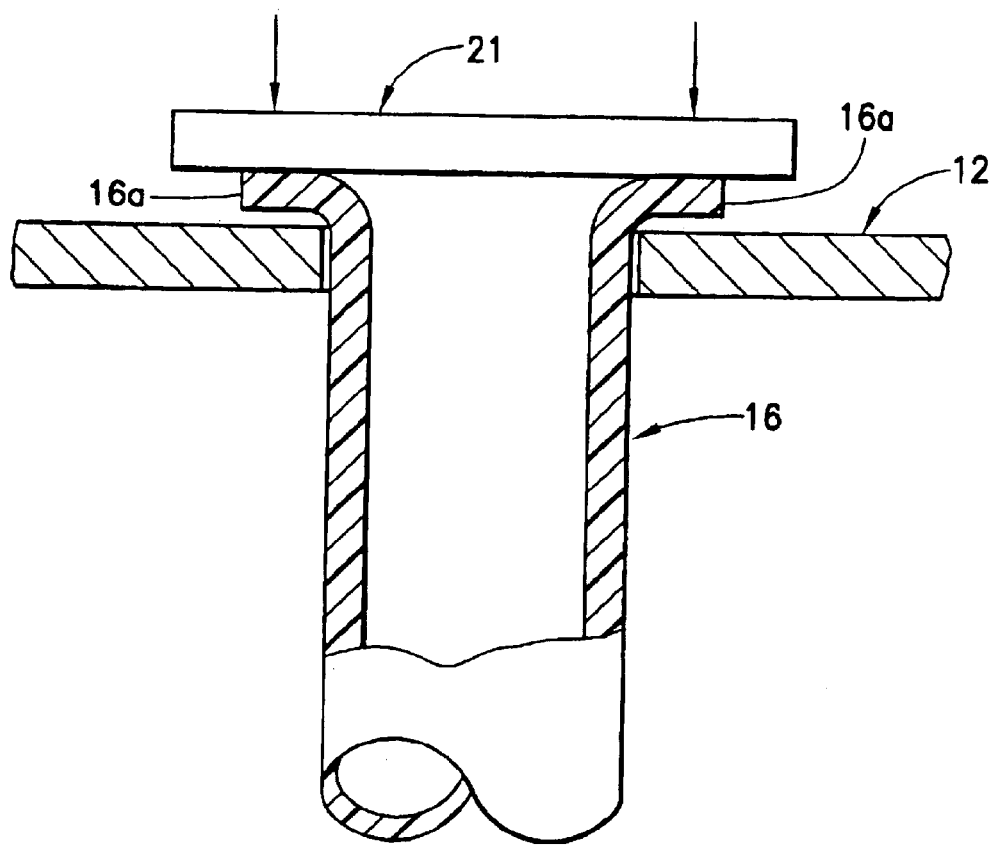
FIG. 7 shows a cross sectional view of a component of an artificial intervertebral disc according to an embodiment of the present invention.

In yet another embodiment shown in FIG. 7, the ends of the column 16a are flared after extending through the thickness of the anchor plate such that the outer wall of the column lies against the top surface of the anchor plate 12 and the inner wall of the column faces outward axially. A compression flange 21 is affixed to the top surface of the anchor plate, forming a snug fit between the flange, column, and upper surface of the anchor plate. The flange 21 may be joined to the anchor plate 12 by securing a screw through bores provided in the flange and the anchor plate, or by another suitable arrangement, such as by passing a bolt through bores provided in the flange and the anchor plate and securing the bolt with a washer. When the flange is affixed in this manner, a firm frictional engagement is formed between these components, which locks the columns in place. An identical method of termination may be implemented at the opposite end of the column and bottom surface of anchor plate 14. In order to flare the end of the column, a slit may be provided at the end of the column, which could facilitate its flaring.

In one embodiment the column is constructed of ePTFE. ePTFE is an expanded PTFE that, as a result of the expansion process, possesses a network of nodes (pores), connected by fibrils, that impart certain mechanical properties to the material. For example, it is believed that the amount of force needed to compress the column may remain nearly constant over a given distance, until all of the voids between the nodes and fibrils are nearly compressed. At this point, it is further believed that near the solid height of the ePTFE, the compressive force may increase non-linearly with respect to the axial deflection of the column such that the effective modulus of elasticity of the structure is increasing. Similar behavior may be seen when the column is decompressed in tension. It is believed that when the artificial disc assembly is inserted between vertebral bodies and subjected to customary loads, the artificial disc of this embodiment may perform similar to the way in which a healthy intervertebral lumbar disc will perform.

ePTFE is described in U.S. Pat. No. 3,953,566 as follows "in the case of uniaxial expansion the nodes are elongated, the longer axis of a node being oriented perpendicular to the direction of expansion. The fibrils which interconnect the nodes are oriented parallel to the direction of expansion. These fibrils appear to be characteristically wide and thin in cross-section, the maximum width being equal to about 0.1 micron (1000 angstroms) which is the diameter of the crystalline particles. The minimum width may be 1 or 2 molecular diameters or in the range of 5 or 10 angstroms. The nodes may vary in size from about 400 microns to less than a micron, depending on the conditions used in the expansion. Products which have been expanded at high temperatures and high rates have a more homogeneous structure, i.e. they have smaller, more closely spaced nodes and these nodes are interconnected with a greater number of fibrils. These products are also found to have much greater strength." This patent is incorporated herein by reference.

Referring once again to FIGS. 2A–2E, it is seen that in this embodiment there exists a portion 30, 31 of the anchor plate which is elevated beyond the surface, which elevated portion contacts the surface of the vertebral endplate. This elevated portion of the anchor plate may be the interface between the anchor plate and the vertebral body. The elevated interface may reside in a corresponding depression or groove formed in the vertebral endplate. The elevated interface may be furnished with an undercut 35, 36 to provide a dovetail fit between the anchor plate and the depression or groove that is formed in the vertebral body. This arrangement may facilitate the initial fixation of the AID device, by allowing the assembly to slide into place, or for ultimate fixation, by allowing bone to grow into the undercut region of the interface feature on the anchor plate. In one embodiment, the undercut 35, 36 may run linearly down the sides of the elevated portion, as in FIGS. 2A–2E. In yet another embodiment, the undercut 35, 36 may run down the center of the plate, as shown in FIGS. 4A–4E, in a configuration, which in its cross section (see FIG. 4C) resembles a light bulb, with a neck portion and a bulbous portion. In yet another embodiment, the undercut 35,36 may pass around the perimeter of the opening in the anchor plate, such as the daisy wheel configuration of FIGS. 3A–3D, or intersect linearly with a truncated daisy wheel configuration as in FIGS. 5A–5E.

The elevated interface may be provided on the anchor plate in order to form an interface between the vertebral bodies and the surface of the anchor plates. That is, over a period of time, the vertebral bodies may grow around the interface on each of the anchor plates, forming a complementary arrangement, which anchors the implant in place.

The artificial disc may be designed such that in addition to allowing for anterior implantation, it may be implanted posteriorly (i.e., the surgeon can implant the assembly from the backside of the patient).

In this regard it is noted that during the surgical procedure, the surgeon may make the requisite incisions or access the site where the unhealthy or damaged disc is to be removed. After removal of the unhealthy or damaged disc, the surgeon may cut grooves in the endplates of the vertebral bodies that were adjacent to the removed disc. The grooves that are cut may be sized and shaped to correspond to the interface on the elevated portion of the anchor plate.

The compressibility of the implant of the present invention may prove helpful during the implanting procedure. As the implant is being inserted between the vertebrae, the implant may be compressed to smaller proportions than its uncompressed height. The surgeon can then, prior to releasing the implant from its compressed height, adjust its position to insure that the elevated interface on the anchor plates and the grooves cut into the vertebral bodies are aligned with each other. After the surgeon has ensured this is the case, the implant may be released from its compressed state, so that the elevated interface enters the grooves.

Alternatively, the grooves may be cut in the vertebral body with a matching undercut, such that the anchor plates may be inserted from the side in a dovetail configuration. This embodiment may allow for positive initial tensile attachment between the anchor plates and the endplates, without having to wait for bony ingrowth.

Referring once again to attachment of the column(s) to the anchor plate(s), it is noted that techniques other than (or in addition to) those described above may be employed. For example, an intermediate design element may be employed whereby the intermediate design element may be joined to the column by, for example, ultrasonic welding, heat sealing (i.e., fusion welding) and/or chemical bonding (thus forming a column assembly). The intermediate design element may be constructed of ePTFE, PTFE, or another chemically compatible material. Once the column assembly has been formed, it may be attached to the anchor plate such that there exists a structurally sound connection.

In one embodiment, the ePTFE column is a hollow column. In another embodiment the column is filled with an elastomeric material, such as silicone or urethane.

In yet another embodiment, the ePTFE column contains a spring element, such as a titanium spring.

Of note, the physical properties exhibited by the columns may be modified by changing the physical dimensions of the cross section of the column, and/or by varying the density of the nodes of the ePTFE. This may alter the static, dynamic, and or kinematic behavior of the material.

In another embodiment the columns of ePTFE may be coated with a silicone or other biocompatible elastomer layer. Such a coating layer may prohibit the growth of tissue and/or bone within the interstices of the nodes, between the fibrils in the column. In another embodiment the elastomer may be extruded onto the column.

As shown in the Figures, the anchor plates may be disposed in a non-parallel configuration (in order to account for the lordotic angle of the vertebrae, for example). This will help insure that the surface of the anchor plate will contact a respective surface of the vertebral bodies to the fullest possible extent. An AID constructed in this manner may exhibit behavior similar to that of the original disc, which also reflected the lordotic angle between vertebral bodies. In one specific example, the angle may lie in the range of 5° to 15°, which should cover the lordotic angles of the vertebral bodies of most of the population.

In another embodiment the anchor plates may be constructed of a strong durable material that is biocompatible. A material which has gained widespread acceptance in constructing in vivo implants is titanium 6AL 4V ELI (extra low interstitial), an alloy containing 6% aluminum and 4% vanadium. One of ordinary skill in the art would readily appreciate the other materials that could be used to construct implants according to the present invention.

Figure 5C:
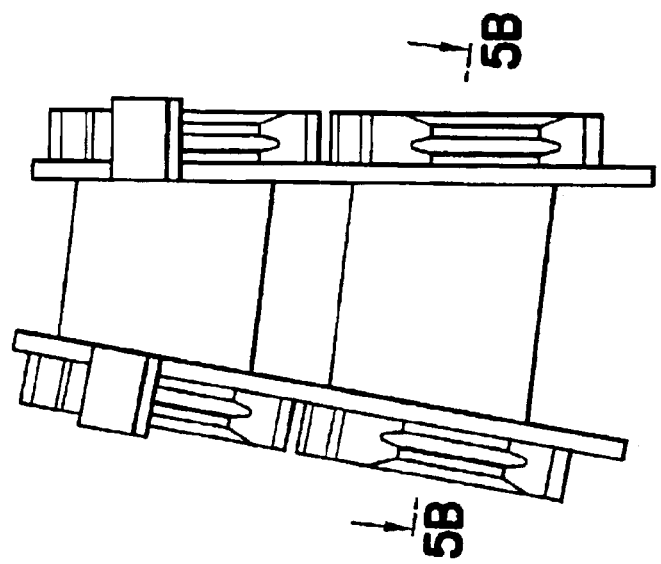
FIG. 5C shows a side elevation view along another side of a component of an artificial intervertebral disc according to an embodiment of the present invention.
Figure 5B:
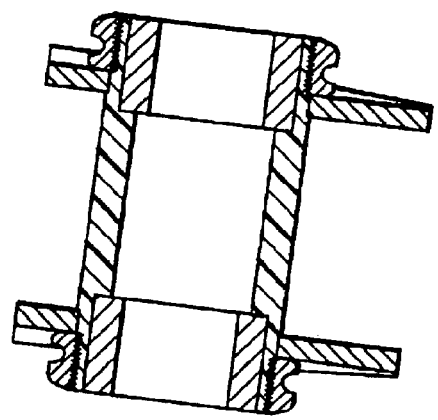
FIG. 5B shows a cross sectional view of a component of an artificial intervertebral disc according to an embodiment of the present invention.
Figure 5A:
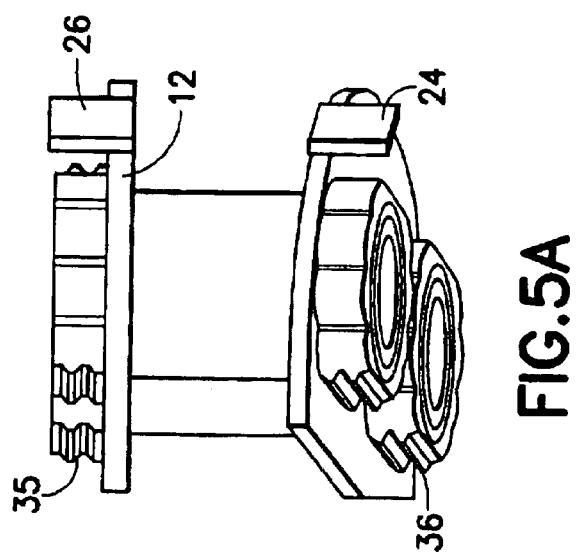
FIG. 5A shows a side elevation view along one side of a component of an artificial intervertebral disc according to an embodiment of the present invention.
Figure 5E:
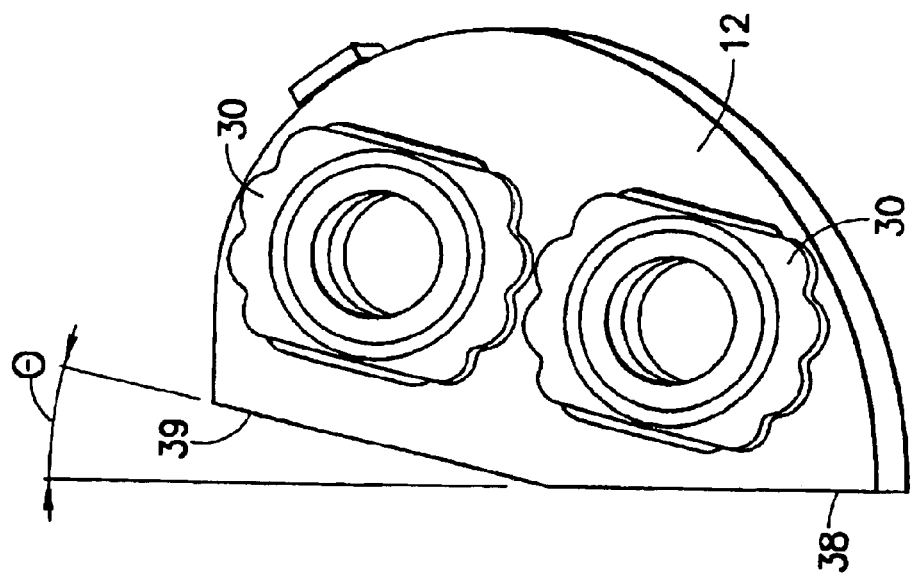
FIG. 5E shows a top plan view of a component of an artificial intervertebral disc according to an embodiment of the present invention.
Figure 5D:
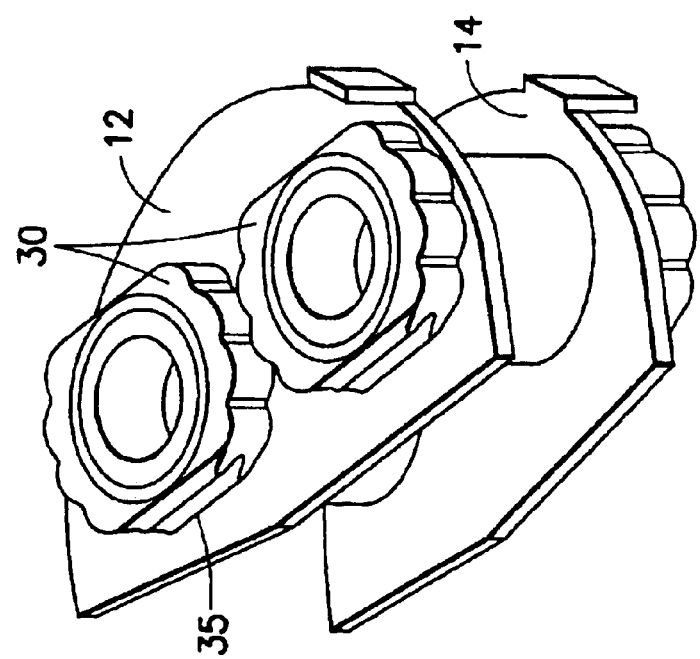
FIG. 5D shows a perspective view of a component of an artificial intervertebral disc according to an embodiment of the present invention.

Referring now to FIGS. 2E and 5E, for example, it can be seen that anchor plate edges 38 and 39 may form angle θ. This angle may be provided to account for the angle at which the device enters the body. That is, the angle may be provided as a design feature in order to facilitate installation by particular approach, such as a posterior lateral approach, for example. Thus, the device may be designed to have a preselected angle θ that facilitates a particular approach to installation.

Figure 6:
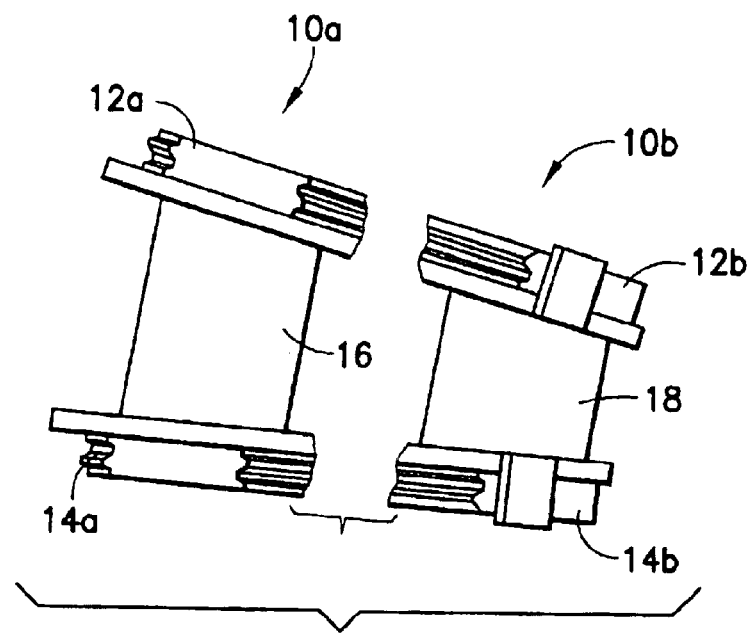
FIG. 6 shows a side elevational view of another embodiment of the present invention in which the artificial intervertebral disc is comprised of a pair of implant components.

FIG. 6 shows another embodiment of the present invention in which the artificial intervertebral disc is comprised of a pair of implant components (or assemblies) 10a,10b. Each component (or assembly) 10a,10b is provided with anchor plates 12a, 14a, 12b, 14b, and columns 16, 18, joined to the anchor plates in the manners previously discussed. The implant components (or assemblies) may be provided with matching lordotic profiles and may be intended to sit laterally adjacent to each other. This arrangement may provide flexibility in the insertion process, allowing one component to be inserted from each side of the spinal cord, for example.

FIG. 8 shows another embodiment of the present invention in which the implant is comprised of a pair of implant components (or assemblies) 10a,10b. Each component (or assembly) 10a,10b is provided with anchor plates 12a, 14a, 12b, 14b, and columns 16a, 18a, 16b, 18b joined to the anchor plates in the manners previously discussed. The implant components (or assemblies) may be provided with matching lordotic profiles and may be intended to sit laterally adjacent to each other. This arrangement may provide flexibility in the insertion process, allowing one component to be inserted from each side of the spinal cord, for example. Of note, this FIG. 8 shows an embodiment comprised of one component (or assembly) similar to the one shown in the views of FIGS. 5A–5E and another component (or assembly) also similar to the one shown in the views of FIGS. 5A–5E, but with an essentially mirror-image configuration (multi-component (or multi-assembly) implants corresponding to embodiments shown in the other Figures are, of course, also contemplated by the present invention).

Turning now to FIGS. 1 to 8, the perimeters of the anchor plates may be provided with tabs 24, 26 that extend at an angle substantially normal to the plane of the anchor plates. The tabs 24, 26 have an outer surface and an inner surface that faces in toward the anchor plates. The tabs 24 may aid in attaining the correct positioning of the implant relative to the vertebral bodies it is positioned between. The correct position may be attained when the inner surface of the tabs 24, 26 lie substantially flush against the outer surface of the vertebral bodies. Optionally, the tabs 24, 26 may be provided with through bores, through which fixation devises, such as bone screws, may be inserted in order to lock the implant in place.

In yet another embodiment, the column of ePTFE maybe a solid chord of material. In another embodiment, the ePTFE may be provided with non-expanded regions, such as at the anchoring regions, for example In a further embodiment, the columns of ePTFE could be extruded to have greater wall thickness on one side or end as opposed to another side or end. For example, the walls of the anterior tube side may be extruded thicker than the walls of the posterior tube side.

In yet another embodiment, the device may be shaped as desired, such as having an oval shape or a kidney shape, for example. This could be effected by providing a desired shape to the anchor plates and/or the column(s).

The structural features of the invention, and methods for installing them, and for stabilizing the device, have been described. Of note, the implants of the present invention may provide one or more of the following attributes when inserted in the body (e.g., between vertebrate):

Essentially the same articulation as a healthy intervertebral disc (e.g., intervertebral lumbar disc) may be realized;

Essentially the same kinematic behavior as a healthy intervertebral disc (e.g., intervertebral lumbar disc) may be realized;

Essentially the same dynamic behavior as a healthy intervertebral disc (e.g., intervertebral lumbar disc) may be realized;

The static properties of the implant and a healthy intervertebral disc (e.g., intervertebral lumbar disc) may be substantially identical;

The implant may be biocompatible;

The device may be implanted by posterior or anterior approaches;

The device may install in a relatively short period of time (e.g., around 90 minutes);

The device may exhibit positive results in fatigue tests (i.e., the device may be usable after $10 \times 10^6$ cycles);

The device may survive static loading, shear loading and testing to induce expulsion;

The device may fixate rapidly to vertebral bodies;

The device may minimize contact stress with vertebral bodies at the device interface; and The device may be auto-clavable.

While a number of embodiments of the present invention have been described, it is understood that these embodiments are illustrative only, and not restrictive, and that many modifications may become apparent to those of ordinary skill in the art.

What is claimed is:

1. An artificial intervertebral disc for implantation in a spine between a first vertebral body and a second vertebral body, wherein the first vertebral body has a first vertebral body endplate, the second vertebral body has a second vertebral body endplate and the first vertebral body endplate and the second vertebral body endplate oppose one another, comprising:
   a composite structure, which composite structure includes a column comprising ePTFE and a column filler comprising an elastomer;
   a first anchor member having an outer surface configured for placement against the first vertebral body endplate and an inner surface having a recess for receiving the composite structure, including both the ePTFE column and the elastomer column filler;
   a second anchor member having an outer surface configured for placement against the second vertebral body endplate and an inner surface having a recess for receiving the composite structure, including both the ePTFE column and the elastomer column filler;
   wherein the composite structure is attached to the first anchor member in the recess in the inner surface of the first anchor member; and
   wherein the composite structure is attached to the second anchor member in the recess in the inner surface of the second anchor member.

2. The artificial intervertebral disc of claim 1, wherein the composite structure is configured such that the composite structure has associated therewith, in at least one axis, a load versus deflection behavior substantially similar to that of a substantially healthy human intervertebral disc.

3. The artificial intervertebral disc of claim 2, wherein the load versus deflection behavior is selected from the group consisting of: (a) dynamic behavior, which dynamic behavior is a function of a time rate application of load, (b) kinematic behavior; and (c) static behavior.

4. The artificial intervertebral disc of claim 2, wherein the load versus deflection behavior includes a non-linear relationship between an amount of force required to compress the composite structure and a deflection of the composite structure.

5. The artificial intervertebral disc of claim 4, wherein a stiffness of the composite structure increases as the composite structure is compressed.

6. The artificial intervertebral disc of claim 2, wherein the column has a hole therethrough.

7. The artificial intervertebral disc of claim 6, wherein at least one of the column and the hole in the column has a substantially circular cross-section.

8. The artificial intervertebral disc of claim 7, wherein each of the column and the hole in the column has a substantially circular cross-section.

9. The artificial intervertebral disc of claim 8, wherein the column filler is disposed within the hole in the column.

10. The artificial intervertebral disc of claim 9, wherein the elastomer is selected from the group consisting of: (a) a silicone, (b) a urethane, and (c) a thermoplastic elastomer.

11. The artificial intervertebral disc of claim 6, wherein the composite structure is attached at a first end of the composite structure to the first anchor member and the composite structure is attached at a second end of the composite structure to the second anchor member.

12. The artificial intervertebral disc of claim 11, wherein the composite structure is attached to each of the first anchor member and the second anchor member by a mechanism selected from the group consisting of:
   (a) compressing a portion of the column radially between a compression ferrule fitted in the hole in the column and a first mating surface of a respective one of the first anchor member and the second anchor member, which first mating surface is formed by a hole through a respective one of the first anchor member and the second anchor member, and
   (b) flaring an end of the column and compressing the flared portion of the column between a capturing component and a second mating surface of a respective one of the first anchor member and the second anchor member.

13. The artificial intervertebral disc of claim 12, wherein the flaring the end of the column and compressing the flared portion of the column between the capturing component and the second mating surface of the respective one of the first anchor member and the second anchor member comprises inserting the column through the hole in a respective one of the first anchor member and the second anchor member before the end of the column is flared.

14. The artificial intervertebral disc of claim 12, wherein the capturing component is attached to a respective one of the first anchor member and the second anchor member by a mechanism selected from the group consisting of:
   (a) a mechanism for threading the capturing component to a respective one of the first anchor member and the second anchor,
   (b) a mechanism for adhesively bonding the capturing component to a respective one of the first anchor member and the second anchor member,
   (c) a mechanism for press-fitting the capturing component to a respective one of the first anchor member and the second anchor member, and
   (d) a mechanism for affixing the capturing component to a respective one of the first anchor member and the second anchor member via at least one threaded fastener.

15. The artificial intervertebral disc of claim 6, wherein the column has a first end and a second end and at least one end of the column is attached to a flange by a mechanism selected from the group consisting of: (a) fusion welding, (b) chemical bonding, and (c) ultrasonic welding.

16. The artificial intervertebral disc of claim 15, wherein the column is treated with a material which aids in the attachment to the flange, which treatment is selected from the group consisting of: (a) impregnating the column with the material, and (b) coating the column with the material.

17. The artificial intervertebral disc of claim 15, wherein the flange is attached to at least one of the first anchor member and the second anchor member by a mechanism selected from the group consisting of:
   (a) capture behind a press-fit capture ring,
   (b) threading the flange onto at least one of the first anchor member and the second anchor member, and
   (c) attaching the flange to at least one of the first anchor member and the second anchor member via at least one threaded fastener.

18. The artificial intervertebral disc of claim 1, wherein the column is impregnated with a material selected from the group consisting of: (a) a material that aids in preventing biological ingrowth into the column, and (b) a material that aids in preventing biological attachment to the column.

19. The artificial intervertebral disc of claim 1, wherein the column is coated with a material selected from the group consisting of: (a) a material that aids in preventing biological ingrowth into the column, and (b) a material that aids in preventing biological attachment to the column.

20. The artificial intervertebral disc of claim 1, wherein the artificial intervertebral disc is configured to be implanted by at least one method selected from the group consisting of: (a) posterior implantation; and (b) anterior implantation.

21. An artificial intervertebral disc, comprising:
   a first anchor member;
   a second anchor member; and
   at least two composite structures disposed side-by-side adjacent one another between the first anchor member and the second anchor member, wherein a first one of the composite structures is attached to both the first anchor member and the second anchor member and is comprised of a first column formed of ePTFE and a first column filler formed of an elastomer and wherein a second one of the composite structures is attached to both the first anchor member and the second anchor member and is comprised of a second column formed of ePTFE and a second column filler formed of an elastomer.

22. The artificial intervertebral disc of claim 21, wherein the first composite structure and the second composite structure are configured such that the first composite structure and the second composite structure have associated in combination therewith, in at least one axis, a load versus deflection behavior substantially similar to that of a substantially healthy human intervertebral disc.

23. The artificial intervertebral disc of claim 22, wherein the load versus deflection behavior is selected from the group consisting of: (a) dynamic behavior, which dynamic behavior is a function of a time rate application of load, (b) kinematic behavior, and (c) static behavior.

24. The artificial intervertebral disc of claim 22, wherein the load versus deflection behavior includes a non-linear relationship between an amount of force required to compress the first composite structure and the second composite structure and a deflection of the first composite structure and the second composite structure.

25. The artificial intervertebral disc of claim 24, wherein a stiffness of each of the first composite structure and the second composite structure increases as each of the first composite structure and the second composite structure is compressed.

26. The artificial intervertebral disc of claim 21, wherein the artificial intervertebral disc is configured to be implanted by at least one method selected from the group consisting of: (a) posterior implantation, and (b) anterior implantation.

27. An artificial intervertebral disc for implantation in a spine between a first vertebral body and a second vertebral body, wherein the first vertebral body has a first vertebral body endplate, the second vertebral body has a second vertebral body endplate and the first vertebral body endplate and the second vertebral body endplate oppose one another, comprising:
   a first assembly including:
   (a) a first anchor member;
   (b) a second anchor member; and
   (c) a composite structure disposed between the first anchor member of the first assembly and the second anchor member of the first assembly, wherein the composite structure of the first assembly is attached to both the first anchor member of the first assembly and the second anchor member of the first assembly, and the composite structure of the first assembly includes a column comprised of ePTFE and a column filler comprised of an elastomer; and
   a second assembly including:
   (a) a first anchor member;
   (b) a second anchor member; and
   (c) a composite structure disposed between the first anchor member of the second assembly and the second anchor member of the second assembly, wherein the composite structure of the second assembly is attached to both the first anchor member of the second assembly and the second anchor member of the second assembly, and the composite structure of the second assembly includes a column comprised of ePTFE and a column filler comprised of an elastomer;
   wherein the first assembly and the second assembly are disposed side-by-side adjacent one another between the first vertebral body endplate and the second vertebral body endplate.

* * * * *